United States Patent
Patel et al.

(10) Patent No.: US 6,736,861 B2
(45) Date of Patent: May 18, 2004

(54) METHOD AND COMPOSITION FOR THE GRADUAL PERMANENT COLORING OF HAIR

(75) Inventors: Jitendra Patel, Fox River Grove, IL (US); Gerald Patrick Newell, Hoffman Estates, IL (US)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 2 days.

(21) Appl. No.: 10/196,130

(22) Filed: Jul. 17, 2002

(65) Prior Publication Data

US 2003/0074748 A1 Apr. 24, 2003

Related U.S. Application Data

(63) Continuation of application No. 09/811,920, filed on Mar. 19, 2001, now abandoned.

(51) Int. Cl.⁷ .................................. A11K 7/13
(52) U.S. Cl. .................. 8/405; 8/406; 8/408; 8/410; 8/411; 8/412; 8/424; 8/435; 8/540; 8/580; 8/581; 8/611
(58) Field of Search ............ 8/405, 406, 408, 8/410, 411, 412, 424, 435, 611, 540, 580, 581, 606

(56) References Cited

U.S. PATENT DOCUMENTS

| | | | |
|---|---|---|---|
| 3,816,615 A | 6/1974 | Zeffren et al. ............... 424/62 |
| 3,912,446 A | 10/1975 | Zviak et al. ................. 8/10.1 |
| 3,931,912 A | 1/1976 | Hsiung ...................... 222/94 |
| 4,096,243 A | 6/1978 | Feinland et al. ............. 424/62 |
| 4,104,021 A * | 8/1978 | Lapidus et al. .............. 8/10.2 |
| 4,297,098 A | 10/1981 | Dasher et al. ................ 8/412 |
| 4,369,037 A | 1/1983 | Matsunaga et al. ........ 8/127.51 |
| 4,402,700 A | 9/1983 | Feinland et al. .............. 8/416 |
| 4,529,404 A | 7/1985 | Feinland et al. .............. 8/406 |
| 4,566,876 A | 1/1986 | Brown et al. ................. 8/411 |
| 4,656,043 A | 4/1987 | Hawkins et al. ............. 424/70 |
| 4,749,565 A | 6/1988 | Grollier ..................... 424/70 |
| 4,925,666 A | 5/1990 | Decker, Jr. et al. ......... 424/401 |
| 4,943,430 A * | 7/1990 | Hefford et al. .............. 424/70 |
| 5,008,105 A | 4/1991 | Grollier et al. ............. 424/70 |
| 5,049,377 A | 9/1991 | Lamb et al. ................ 424/70 |
| 5,064,441 A | 11/1991 | Kawase et al. ............... 8/405 |
| 5,089,257 A | 2/1992 | Schrader et al. ............ 424/70 |
| 5,102,655 A | 4/1992 | Yoshihara et al. ............ 424/62 |
| 5,116,388 A | 5/1992 | Brooks ....................... 8/405 |
| 5,130,124 A | 7/1992 | Merianos et al. ............ 424/53 |
| 5,221,286 A | 6/1993 | Singleton et al. ............. 8/406 |
| 5,376,146 A * | 12/1994 | Caspenson et al. ............ 8/408 |
| 5,393,305 A | 2/1995 | Cohen et al. ................. 8/406 |
| 5,554,197 A | 9/1996 | Assini et al. ................. 8/406 |
| 5,556,615 A | 9/1996 | Janchitraponvej et al. ..... 424/70.11 |
| 5,560,750 A | 10/1996 | Crews et al. ................. 8/431 |
| 5,730,966 A | 3/1998 | Torgerson et al. ......... 424/70.11 |
| 5,849,042 A | 12/1998 | Lim et al. ................... 8/408 |
| 5,942,216 A | 8/1999 | Herb et al. .............. 424/70.28 |
| 5,968,486 A | 10/1999 | Newell et al. ............... 424/62 |
| 5,993,491 A | 11/1999 | Lim et al. ................... 8/409 |
| 6,022,381 A | 2/2000 | Dias et al. ................... 8/406 |
| 6,074,438 A | 6/2000 | Lim et al. ................... 8/409 |
| 6,082,588 A | 7/2000 | Markey et al. ............. 222/137 |
| 6,143,286 A | 11/2000 | Bhambhani et al. ......... 424/701 |
| 6,309,426 B1 | 10/2001 | Dias et al. ................... 8/407 |
| 2001/0002254 A1 * | 5/2001 | Duffer et al. .............. 424/70.1 |
| 2003/0028979 A1 | 2/2003 | Duffer et al. ................. 8/406 |

FOREIGN PATENT DOCUMENTS

| | | | |
|---|---|---|---|
| DE | 2 217 388 | 4/1972 | |
| DE | 27 04 343 A1 | 8/1977 | |
| DE | 100 51 774 | 10/2000 | |
| EP | 0 146 350 | 12/1984 | |
| EP | 0146350 A2 | 6/1985 | |
| EP | 0 146 350 * | 6/1985 | ............ A61K/7/13 |
| EP | 0 823 250 | 12/1996 | |
| EP | 0 823 250 A2 * | 2/1998 | ............ A61K/7/06 |
| FR | 2 802 089 | 12/1999 | |
| GB | 1 289 712 | * of 1872 | |
| GB | 1 289 712 | 9/1972 | |
| WO | 00/10515 | 3/2000 | |
| WO | 01/76545 | 10/2001 | |
| WO | 01/76546 | 10/2001 | |
| WO | 02/074266 | 9/2002 | |

OTHER PUBLICATIONS

Derwent Abstract, XP 002236077 & JP 54 070442 A, dated Jun. 1979.

* cited by examiner

*Primary Examiner*—Eisa B. Elhilo
(74) *Attorney, Agent, or Firm*—Milton L. Honig

(57) ABSTRACT

A method for permanently dyeing hair which comprises subjecting said hair to a number of treatments, having a set time interval between each two consecutive such treatments, wherein each treatment comprises steps a.) and b.) below:

a.) contacting said hair, for a period of about 5 seconds to about 5 minutes with a recently made mixture of:
  i.) an alkaline composition comprising a dye intermediate in a shampoo base or in a conditioner base; and
  ii.) an acidic composition comprising an oxidating compound in a shampoo base or in a conditioner base;

b.) rinsing said mixture from said hair with water;

with the proviso that when a conditioner base is present in a.) i.) above, an independently selected conditioner base is also present in a.) ii.) above; and when a shampoo base is present in a.) i.) above, an independently selected shampoo base is also present in a.) ii.) above;

and wherein said number of treatments is between about 2 to about 30; and wherein said set time interval between each two consecutive treatments is between about 8 hours and 30 days, is described.

23 Claims, No Drawings

METHOD AND COMPOSITION FOR THE GRADUAL PERMANENT COLORING OF HAIR

This is a continuation of Ser. No. 09/811,920, filed Mar. 19, 2001 now abandoned.

BACKGROUND OF THE INVENTION

The present invention relates to a method for the permanent coloring of hair with longer lasting conditioning and with minimized hair damage.

Most hair coloring products fall under three major groupings:

1. Temporary hair color
2. Semi permanent hair color
3. Permanent hair color

Temporary color is a leave on product that causes minimal damage to the hair. However, temporary color causes stains, and leaches out under rain or with perspiration. Temporary color washes out with the next shampoo. Temporary color also does not give any control to the consumer over the amount of color deposited or the permanency of the color supplied. Temporary color does not result in a wide variety of colors and it has only a limited appeal.

Semi-permanent hair color comes as a rinse, and it causes minimal damage to the hair. However, semi-permanent hair color washes out to some degree with each shampoo and washes out completely within about 4 to 6 shampoos. Semi permanent hair color does not give the consumer any control regarding the amount of color deposited or the permanency of the color. Semi-permanent hair color has limited popularity with consumers.

Permanent hair color generally comes in two parts: a dye solution and a developer solution. Because of the damaging nature of current permanent dye treatments, most home coloring products come with a post treatment conditioner. In a permanent hair coloring treatment, the dye solution and the developer solution are mixed and then applied to the hair, which is then left for about 25 to about 35 minutes. The hair is then rinsed with water, treated with a post treatment conditioner, and then rinsed again with water.

The application of the dye solution and the developer solution affords permanent hair coloring. However, this method does not provide any conditioning benefit. The conditioning benefit comes through application of the post treatment conditioner, and it is only temporary. The conditioning benefit is lost with the next shampoo. Moreover, with permanent hair coloring treatments, shampooing the hair is usually not recommended after said treatments. Thus, hair is left feeling dirty, and can stain towels and pillows.

Coloring products need to be applied every four to six weeks since hair grows out of the scalp at the rate of approximately one half inch per month. Each coloring application causes damage to the hair, and that damage is cumulative. Hair touch ups after the initial treatment would also damage hair more.

It would be desirable to develop a method for permanently coloring hair that conditions hair, gives hair a soft clean feel, and minimizes the damage caused to hair by the coloring process. The present invention provides such a method.

Current hair coloring products cannot be used safely in the shower. It is an object of this invention to develop a method for permanently coloring hair, which can be carried out safely in the shower. It is also an object of the invention to provide a method for permanently coloring hair wherein the user has control of the amount of durable color deposited without hair damage. It is also an object of the invention to provide a method for permanently coloring hair wherein the user has control on the amount of lifting/lightening without causing hair damage. It is also an object of the invention to provide a method for permanently coloring hair wherein the user can employ the product as her daily hair care product to avoid new out growth of uncolored hair. It is also an object of the invention to provide a method for permanently coloring hair wherein said method involves less mess and difficulty than conventional permanent hair coloring methods. It is also an object of the invention to provide a method for permanently coloring hair wherein said method brings about gradual color changes with each application. Since gradual color changes are to occur, such a method would be virtually mistake free because the consumer could stop or alter the coloring method if she did not like the course the hair coloring was taking. It is also an object of the invention to provide a method for permanently coloring hair wherein the amount of hair coloring composition employed can be varied from application to application in order to adjust the hair coloring results.

These and other aspects of this invention will become evident by a detailed description of the invention given below.

Patents related to the field of this invention are as follows:

U.S. Pat. No. 4,104,021 which discloses a process in which human hair is dyed in successive treatments at selected intervals with oxidation colors (aromatic primary amines and amino phenols) admixed in each treatment with an oxidizing agent ($H_2O_2$ or a derivative thereof)—the quantity of oxidation colorant applied in each treatment being substantially the same and the quantity of oxidizing agent being increased from the first to the last treatment to effect a gradual increase in depth of shade—the mixture being allowed to remain on the hair for substantially the same time in each treatment, followed by removal by rinsing.

U.S. Pat. No. 4,529,404 discloses an autoxidizable hair dye preparation capable of coloring or darkening hair when applied thereto and exposed to the atmosphere comprising a mixture of (I) at least one p-phenylene diamine compound, or An acid addition salt thereof, and (II) at least one 1,2,4-benzenetriol compound, each compound optionally containing nuclearly substituted C.sub.1–4 alkyl, alkoxy, hydroxyalkyl or halogen. The preparation is preferably applied and exposed to the atmosphere repeatedly until the desired degree of darkening or color build-up is attained.

The preparations of this invention may also contain known additives or assistants such as hair grooming agents, for example quaternized vinyl pyrrolidone copolymers, carboxyvinyl polymers and the like, plasticizers, conditioners, thickeners, slip and wetting agents such as polyoxyethylenated fatty (e.g. lauryl) alcohols, stearyidimethylammonium chloride, silicone copolymer, foam boosters, preservatives, perfumes and the like.

U.S. Pat. No. 5,968,486 describes a shampoo composition for lightening and highlighting hair which comprises (i) a peroxygen compound; and
(ii) an anionic sulfonate;

said composition having a pH less than 5. There is also described an invention directed to a method for lightening and highlighting hair which comprises shampooing the hair with a lightening and highlighting effective amount of a composition of the invention.

U.S. Pat. No. 6,274,126 discloses a hair conditioning composition for conditioning, lightening, and highlighting hair, which comprises i) peroxygen compound, and ii) a conditioning agent, said composition having a pH of 5 or less.

SUMMARY OF THE INVENTION

The invention relates to a method for achieving permanent desired hair color change through the use of daily hair care compositions. The daily hair care compositions comprise a mixture of two compositions, part A and part B as described just below:

Part A: Dye intermediates in a conditioner or shampoo base at alkaline pH

Part B: Hydrogen peroxide in a conditioner or shampoo base at acidic pH

The present invention relates to specific compositions which are a mixture of part A' and part B' as described just below.

Part A: Dye intermediates in a conditioner or shampoo base at alkaline pH

Part B: Hydrogen peroxide in a conditioner or shampoo base at acidic pH

In the case of compositions in a conditioner base, Part A comprises from
- a) about 0.1 to about 99.9% of a conditioning base, wherein the conditioning agent within said conditioning base comprises from about 0.5 to about 10% of the total composition % of a conditioner;
- b) about 0.1 to about 5% of oxidation dyestuffs;
- c) about 0.1 to about 5% of a coupling compound.

More preferably, in the case of compositions in a conditioner base, part A can comprise from
- a) about 1 to about 5% of a conditioning agent;
- b) about 0.1 to about 0.5% of dye;
- c) about 0.1 to about 1% coupling compound.

For compositions in a conditioner base, Part B comprises from: More preferably, in the case of compositions in a conditioner base, part A can comprise from
- a) about 1 to about 5% of a conditioning agent;
- b) about 0.1 to about 0.5% of dye;
- c) about 0.1 to about 1% coupling compound.

More preferably for compositions in a conditioner base, Part B comprises from:
- a) about 1 to about 5% of a conditioning agent; and
- b) about 1 to about 5% of an oxidizing compound.

For compositions in a shampoo base part A comprises:
- a) about 0.1 to about 99.9% of a shampoo base, wherein the detergent foaming agent within said shampoo base comprises from about 0.5 to about 50% of the total composition. % of a shampoo agent;
- b) about 0.1 to about 5% of oxidation dyestuffs;
- c) about 0.1 to about 5% of a coupling compound.

More preferably, in the case of compositions in a shampoo base, part A can comprise from
- a) about 2 to about 15% of a detergent foaming agent;
- b) about 0.1 to about 0.5% of dye;
- c) about 0.1 to about 1% coupling compound.

For compositions in a shampoo base part B comprises:
- a) about 0.5 to about 50% of a detergent foaming agent; and
- b) about 1 to about 5% of an oxidizing compound.

More preferably, in the case of compositions in a shampoo base, part A can comprise from
- a) about 1 to about 15% of a detergent foaming agent; and
- b) about 1 to about 5% of an oxidizing compound.

Specific conditioner bases of the invention, part A, comprise about 0.5 to about 0.5 to about 5% of a quaternary nitrogen-containing conditioning agent having two long aliphatic chains each of which contains about 12 to about 18 carbons and two short chain alkyl groups having one or two carbon atoms each bonded to quaternary nitrogen, 10% higher molecular weight fatty alcohols such as cetyl alcohol and stearyl alcohol; and about 1% to about 4% of a volatile silicone such as dimethicone and the dyestuff.

Shampoo compositions of the invention comprise from about 0.5 to about 50% of an anionic surfactant or an amphoteric surfactant or mixtures thereof.

Conditioning compositions of the present invention comprise a mixture of part A and part B wherein:

Part A comprises:
- a) about 0.1% to about 99.9% of a conditioning base, which comprises about 0.05% to about 10% of a conditioning agent based upon the total composition;
- b) about 0.1% to about 1% of a dye; and
- c) a volatile silicone;

Part B comprises:
- a) about 1 to about 5% of a conditioning base;
- b) about 1 to about 5% of an oxidative compound.

A conditioning composition of the invention is a composition as described just above, which further comprises in part A, part B, or part A and part B, a thickener which is a high molecular weight fatty alcohol wherein said high molecular weight fatty alcohol is selected from the group consisting of cetyl alcohol and stearyl alcohol.

A shampoo composition for permanently dying hair comprises a mixture of Part A and part B wherein:

Part A comprises:
- a) about 0.1% to about 99.9% of a shampoo base; and
- b) about 0.1% to about 1% of a dye;

Part B comprises:
- a) about 1 to about 5% of a shampoo base;
- b) about 1 to about 5% of an oxidative compound.

A shampoo composition of the invention is as described just above wherein said shampoo base in part A comprises about 5 to about 50%, based on the total part A composition, of an anionic surfactant, an amphoteric surfactant, or a mixture of an anionic surfactant and an amphoteric surfactant.

What follows is a description of the ingredients that can be included in the compositions of the present invention.

Hair Dyes and Hair Coloring Agents

The part A compositions of the present invention include as an essential feature one or more oxidative hair coloring agents. These hair coloring agents are present in compositions of the present invention which have a conditioner base, and compositions of the present invention which have a shampoo base. Such oxidative hair-coloring agents are used in combination with the oxidizing systems of the present invention to formulate permanent hair dye compositions.

Permanent hair dye compositions as defined herein are compositions, which once applied to the hair, are substantially resistant to washout.

Oxidative Dyes

The dye forming intermediates used in oxidative dyes are essentially aromatic diamines, aminophenols and their derivatives. These dye forming intermediates can be classified as; primary and secondary intermediates, couplers and modifiers, and nitro dyes. Primary intermediates are chemical compounds, which by themselves will form a dye upon oxidation. The secondary intermediates, also known as color modifiers or couplers and are used with other intermediates for specific color effects or to stabilize the color. Nitro dyes are unique in that they are direct dyes, which do not require oxidation to dye the hair.

The oxidation dye intermediates, which are suitable for, use in the compositions and processes herein include aromatic diamines, polyhydric phenols, aminophenols and derivatives of these aromatic compounds (e.g., N-substituted derivatives of the amines, and ethers of the phenols). Primary oxidation dye intermediates are generally colorless molecules prior to oxidation. The oxidation dye color is generated when the primary intermediate is 'activated' and subsequently enjoined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Color modifiers (couplers), such as those detailed hereinafter, are preferably used in conjunction with the oxidation dye precursors herein and are thought to interpose themselves in the colored polymers during their formation and to cause shifts in the electronic spectra thereof, thereby resulting in slight color changes. A representative list of oxidation dye precursors suitable for use herein is found in Sagarin, "Cosmetic Science and Technology", Interscience, Special Edition, Volume 2, pages 308 to 310.

It is to be understood that the oxidizing aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, aminophenols, and derivatives thereof, described above as primary dye precursors can also have additional substituents on the aromatic ring, e.g. halogen, aldehyde, carboxylic additional substituents on the amino nitrogen and on the phenolic oxygen, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes and other synthetic and natural Chemical and Physical Behaviour of Human Hair 3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: 'Navarre at chapter 45 by G. S. Kass (pp 841–920); 'cosmetics: Science and Technology' 2nd Edn, Vol II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Specific hair dyes which may be included in the compositions of the invention include m-aminophenol, p-phenylene diamine, p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N,N-bis (4-aminophenyl)-2-propanol; 2-methyl-4-dimethylaminoaniline; p-aminophenol; p-methylaminophenol; 3-methyl-p-aminophenol;2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4-hydroxyethylaminoanisole; aminoethoxy-2,4-diaminobenzene; 2,4-diaminophenoxyacetic acid; 4,6-bis (hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis (hydroxyethylamino)toluene; m-aminophenol; 2-hydroxy-4-carbamoylmethylaminotoluene; m-carbamoylmethyl-aminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol;2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylpheno; 2-dimethylamino-5-aminopyridine; 2,4,5,6-tetra-aminopyrimidine; 4,5-diamino-1-methylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 4-hydroxyindole;

3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Buffering Agents

The coloring compositions of the present invention have a preferred pH in the range of from about 7.5 to about 12, more preferably from about 8 to about 10.

Buffering agents may be present in part A compositions of the present invention which have a conditioner base, and compositions of the present invention which have a shampoo base. Coloring compositions of the present invention may contain one or more hair swelling agents (HSAS) such as urea, to adjust the pH to the desired level. Several different pH modifiers can be used to adjust the pH of the final composition or any constituent part thereof.

Further examples of suitable buffering agents are ammonium hydroxide, urea, ethylamine, dipropylamine, triethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-alginine, lysine, oxylysine and histidine and alkanolamines such as dimethylaminoethanol and aminoalkylpropanediol and mixtures thereof. Also suitable for use herein are compounds that form $HCO_3^-$—by dissociation in water (hereinafter referred to as 'ion forming compounds'). Examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)$ and mixtures thereof.

As herein before described certain alkaline buffering agents such as ammonium hydroxide and monoethylamine (MEA) can also act as hair swelling agents (HSA's) such as urea and the like.

Preferred for use as a buffering agent for the coloring compositions according to the present invention is ammonium hydroxide and/or sodium hydroxide.

In oxidizing and coloring kits comprising a portion of peroxide oxidizing agent, which may be present in either solid or liquid form, such as hydrogen peroxide, a buffering agent solution is required to stabilize hydrogen peroxide. Since hydrogen peroxide is stable in the pH range from 2 to 4, it is necessary to use a buffering agent having a pH within this range. Dilute acids are suitable hydrogen peroxide buffering agents. Phosphoric acid is a preferred agent for buffering hydrogen peroxide solutions.

This pH adjustment can be effected by using well known acidifying agents in the field of treating keratinous fibers, and in particular human hair, such as inorganic and organic acids such as hydrochloric acid, tartaric acid, citric acid, phosphoric acid and carboxylic or sulphonic acids such as ascorbic acid, acetic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, is sodium acetate/acetic acid, disodium hydrogenphosphate/citric acid and sodium chloride/glycine/hydrochloric acid and mixtures thereof.

Solvents

Water is the preferred principal diluent for the compositions according to the present invention. As such, the compositions according to the present invention may include one or more solvents as additional diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

These solvents may be present in compositions of the present invention which have a conditioner base, and in compositions of the present invention which have a shampoo base. These solvents may be present in part A compositions of the invention and part B compositions of the invention.

Surfactant Materials

The compositions of the present invention can additionally contain a surfactant system. Suitable surfactants for inclusion in the compositions of the invention generally have a lipophilic chain length of from about 8 to about 22 carbon atoms. Surfactants which are either amphoteric or anionic or zwitterionic are included in compositions of the present invention which have a shampoo base. In addition, there may be included in shampoo compositions of the present invention, cationic, nonionic or zwitterionic surfactants. Compositions of the invention have a conditioner base can included cationic, nonionic or zwitterionic surfactants. Surfactants may be present in part A and part B compositions of the invention.

(i) Anionic Surfactants

Anionic surfactants suitable for inclusion in the compositions of the invention include alkyl sulphates, ethoxylated alkylsulphates, alkyl glyceryl ether sulfonates, methyl acyl taurates, fatty acyl glycinates, N-acyl glutamates, acylisethionates, alkyl sulfosuccinates, alkyl ethoxysulphosuccinates, alpha-sulfonated fatty acids, their salts and/or theiresters, alkyl ethoxy carboxylates, alkyl phosphate esters, ethoxylated alkyl phosphate esters, alkyl sulphates, acylsarcosinates and fatty acid/protein condensates, and mixtures thereof. Alkyl and/or acyl chain lengths for these surfactants are C12–C22, preferably C12–C18 more preferably C12–C14.

(ii) Nonionic Surfactants

The compositions of the invention can also comprise a water-soluble nonionic surfactants.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives.

Preferred for use herein are polyethyleneglycol based polyethoxylated $C_9$–$C_{15}$ fatty alcohol nonionic surfactants containing an average of from about 5 to about 50 ethyleneoxy moieties per mole of surfactant.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include: alkyl betaines, alkyl sultaines, alkyl amphoacetates, alkyl amphodiacetates, alkyl amphopropionates, and alkyl amphodipropionates.

(iv) Zwitterionic Surfactants

Water-soluble auxiliary zwitterionic surfactants suitable for inclusion in the compositions of the present invention include alkyl betaines Water-soluble auxiliary sultaine surfactants suitable for inclusion in the compositions of the present invention include alkyl sultaines. Preferred for use herein is coco amido propylhydroxy sultaine.

Water-soluble auxiliary amine oxide surfactants suitable for inclusion in the compositions of the present invention include alkyl amine oxide R.sub.5 R.sub.6 R.sub.7 NO and amido amine oxides number from 1 to 4. Preferred amine oxides include cocoamidopropylamine oxide, lauryl dimethyl amine oxide and myristyl dimethyl amine oxide.

(v) Cationic Surfactants

Cationic surfactants include polyethylene condensates of alkyl phenols, condensation products of ethylene oxide, propylene oxide, and ethylene oxide, propylene oxide, and ethylene diamine, long chain tertiary amine oxides, long chain tertiary phosphine oxides, and the like.

Conditioners

The conditioning compositions of this invention also contain at least a water-soluble or water-dispersible quaternary nitrogen-containing conditioning agent that is also sometimes referred to herein as a cationic compound. A long chain fatty alcohol is also present in more preferred compositions, and a tertiary amidoamine is additionally present in particularly preferred compositions.

The quaternary nitrogen-containing conditioning agents are preferably present at from about 0.5 to about 5 percent by weight of the composition as an active ingredient. More preferably, the quaternary nitrogen-containing conditioning agent is present at from about 2 to about 3 weight percent, as an active ingredient.

The class of quaternary nitrogen-containing conditioning agents useful herein contain one quaternary nitrogen atom having (a) two long aliphatic chains and (b) two identical or different short chain alkyl groups having one or two carbon atoms, each bonded to the quaternary nitrogen atom. The two long chains each contain about 12 to about 18 carbon atoms.

Illustrative conditioning agents include distearyidimethylammonium chloride and dilauryldimethylammonium chloride. These compounds are named Quaternium-5 and Quaternium-47, respectively, in the CTFA Cosmetic Ingredient Dictionary, 2nd ed., 1977, published by the Cosmetic, Toiletry and Fragrance Association, Inc., hereinafter referred to as the CTFA Dictionary.

It is noted that the long aliphatic chain of the beforementioned conditioning agents need not be solely or primarily of one chain length, i.e., the long chain need not be cetyl, myristyl, lauryl or stearyl. Rather, conditioning agents whose long aliphatic chain contains a mixture of lengths can be used. Such conditioning agents are conveniently prepared from naturally occurring materials, such as tallow, coconut oil, soya oil and the like, or from synthetically produced mixtures. Examples of useful conditioning agents having mixed aliphatic chain lengths include dimethyldi-(hydrogenated tallow)ammonium chloride and dialkyldimethylammonium chloride wherein each alkyl group is a saturated group consisting primarily of 16 carbon atoms. These quaternary nitrogen-containing conditioning agents are named Quaternium-18 and Quaternium-31, respectively, in the CTFA Dictionary.

The compositions of this invention can also be in the form of emulsions that contain additional amounts of hydrophilic and/or hydrophobic ingredients. Emulsions containing additional hydrophobic materials are particularly preferred. It is preferred that those emulsions be stable to phase separation at a temperature of about 25. degree. C. for a period of about 24 hours after their preparation. The emulsions are more preferably stable to phase separation at temperature normally found in commercial product storage and shipping for periods of one year or more.

Thickeners

Thickeners may be included in compositions of the invention which have a shampoo base, and compositions of the invention which have a conditioner base, and thickeners may be included in part A and part B compositions of the invention. Long chain fatty alcohols having from about 11 to about 18 carbon atoms in the long fatty chain can be thickener constituents of the conditioning emulsions of this invention. These alcohols can be used alone, or in admixture with each other. When included in the compositions, the alcohol is preferably present at from about 0.5 to about 10 weight percent of the composition, and more preferably at from about 2 to about 5 weight percent.

Lauryl alcohol, oleyl alcohol, myristyl alcohol, stearyl alcohol, and the like, and mixtures thereof are contemplated herein. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickeners

Thickening agents suitable for use in the compositions herein may also be selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer that are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Optional Ingredients

The compositions of the present invention can comprise a wide range of optional ingredients. . Examples of these functional classes include: anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and the like.

Other optional ingredients include organic acids. A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. Non-exclusive lists of examples of mineral acid for use herein are hydrochloric, phosphoric, sulfuric and mixtures thereof.

We have found by experimentation that daily hair care products can achieve durable desired hair color. As noted above, the daily hair care product consists of two parts.

Part A: Dye intermediates in a conditioner or shampoo base at alkaline pH

Part B: Hydrogen peroxide in a conditioner or shampoo base at acidic pH

Part A is mixed with part B and applied to hair. The reason current hair coloring products come in two packages is because the mixture of the coloring component and the oxidizing component is unstable and the two components must be kept apart until just before use. Similarly part A and part B of the present invention must be kept apart until just before use. By varying the concentration of the actives and the treatment time, the amount of color on hair could be varied while minimizing hair damage. To make the product more convenient and fool proof, part A and B can be packaged in dual dispensing systems where both parts are mixed out side of the package when dispensed which is then applied to the wet hair as a conditioner or shampoo. Depending upon the amount of color desired, the treatment time could be varied from two minutes or longer.

Such conditioner or shampoo treatments would add color to hair gradually without damage due to lower contact time. Each subsequent treatment would add color until the desired shade is obtained. Depending upon the concentration of the actives and contact time, a desired shade may be reached in six to eight treatments. We have found that since any one treatment does not exceed the threshold of irreversible damage, the total damage resulting from multiple treatments is lower than the damage from a single conventional treatment. Such a process gives the user control on the amount of color deposited on her hair, and also the option to discontinue further applications if the color delivered is not to her liking. She also has the option to switch to another color shade immediately without having to wait the six to eight weeks that is recommended for conventional treatments. With conventional hair color treatment, it is not recommended to perm and color hair simultaneously due to extensive damage. However, since this method colors the hair with minimum damage, perming can be done in the same time frame with this progressive coloring treatment.

The following examples, which were made, are shown as illustrations only and are not intended to limit the scope of the invention:

EXAMPLE #1

| Dark Brown Color conditioner: Part A | |
|---|---|
| DI Water | 70.00 |
| Stearamidopropyl dimethylamine | 0.50 |
| Dicetyldimonium chloride/PG, 68%/27% | 2.10 |
| Stearyl alcohol and Ceteareth-20, 70% | 1.00 |
| Cetyl alcohol | 3.60 |
| DI water | 3.00 |
| Disodium EDTA | 0.10 |
| Dimethicone 100% | 1.00 |
| DC silicone fluid 245 | 1.80 |
| Preservatives | 0.18 |
| DMDM Hydantoin 55% | 0.10 |
| Fragrance A42867H/7454965 | 0.20 |
| Sodium metabisulfite | 0.10 |
| DI water | 15.11 |
| m-Aminophenol | 0.03 |
| N,N Bis(2-hydroxyethyl)-p-phenylenediamine sulfate | 0.13 |
| p-Phenylenediamine | 0.45 |
| o-Aminophenol | 0.05 |
| Resorcinol | 0.25 |
| Sodium hydroxide 50% | 0.40 |

PH = 8 to 9

Manufacturing Process

Weigh the ingredients(item#13 to 18) needed into an appropriate container;

Flush the container(tank) with nitrogen gas;

Add item #1 into a suitable container. Heat to 180–185 F., Keep the Nitrogen blanket;

Add pre-weighed dyes with moderate agitation. Keep the Nitrogen blanket;

Add item #3 with moderate agitation;

Add item #2, 4 and 5, dissolve completely;

Mix batch at approximately 180–185 F. for at least an hour with agitation until particles; are completely dissolved. Check for the particles;

Begin cooling. Keep the nitrogen blanket with moderate agitation;

Prepare EDTA and sodium phosphate solution using item#7 DI water;

At 130 F. add the EDTA solution to the batch;

At 110 F. or below, add items #8, 9, 10, 11, 12; mix well;

Adjust the pH to around 10.0; keep the Nitrogen blanket through entire process;

Qs with DI water.

| Peroxide conditioner: Part B | |
|---|---|
| D.I. Water | 74.00 |
| Liquid Citric acid, 50% | 0.20 |
| Stearamidopropyl dimethylamine | 0.50 |
| Dicetyldimonium chloride/PG, 68%/27% | 2.10 |
| Stearyl alcohol and Ceteareth-20, 70% | 1.00 |
| Cetyl alcohol | 3.80 |

-continued

| Peroxide conditioner: Part B | |
|---|---|
| DI water | 5.00 |
| Disodium EDTA | 0.10 |
| Dimethicone 100% | 1.00 |
| DC silicone fluid 245 | 1.80 |
| Hydrogen Peroxide(35%) | 10.00 |
| DMDM Hydantoin 55% | 0.10 |
| Fragrance A42867H/7454965 | 0.20 |
| Phosphoric acid, 85% | 0.09 |

PH = 2.5 to 3.5

Manufacturing Process

1. Add item#1 into a suitable container. Heat to 180–185 F.
2. Add item#2 with moderate agitation
3. Add item#4, dissolve completely
4. At 165–170 F., add item#3, 5, 6
5. Mix batch at approximately 180–185 F. for at least an hour with agitation until particles are completely dissolved. Check for the particles
6. Begin cooling.
7. In a separate container dissolve item#8 in item#7)
8. At 130 F. add the EDTA solution to the batch.
9. At 110 F. or below, add item#9, 10, 11, 12, and 13 Mix well
10. Adjust the pH with item#14 to 2.7 to 3.0
11. Qs with water Method of Using Above Conditioners Shampoo the hair tresses. Take equal part of color conditioner of part A and B (formula#1), mix and apply to the wet hair tresses, keep for two minutes, and rinse well. Repeat the above procedure for subsequent treatment. Collect the hair tress after 2, 4 and 6 treatments. Measure the change in color delta E using McBeth ColorEye.

The table below summarized the part A formulation for various shades. One can use same peroxide conditioner part B for all shades.

| Ingredients | Hair Color Conditioner: Part A | | | | | |
|---|---|---|---|---|---|---|
| | Dark Brown | Light Brown | Dark Blonde | Light Blonde | Dark Auburn | Light Auburn |
| Composition No. | 65 | 66 | 67 | 68 | 69 | 71 |
| Deionized water | 70.00 | 70.00 | 70.00 | 70.00 | 70.00 | 70.00 |
| Stearmidopropyl dimethylamine | 0.50 | 0.50 | 0.50 | 0.50 | 0.50 | 0.50 |
| Dicetyldimonium chloride | 2.10 | 2.10 | 2.10 | 2.10 | 2.10 | 2.10 |
| Stearyl alcohol and Ceteareth-20 | 1.00 | 1.00 | 1.00 | 1.00 | 1.00 | 1.00 |
| Cetyl alcohol | 3.60 | 3.60 | 3.60 | 3.60 | 3.60 | 3.60 |
| Disodium EDTA | 0.10 | 0.10 | 0.10 | 0.10 | 0.10 | 0.10 |
| Sodium phosphate | — | 0.20 | 0.20 | 0.20 | — | 0.20 |
| Deionized water | 18.41 | 18.65 | 19.32 | 15.00 | 17.99 | 15.00 |
| Fragrance | 0.20 | 0.20 | 0.20 | 0.20 | 0.20 | 0.20 |
| Dimethicone | 0.10 | 0.10 | 0.10 | 0.10 | 0.10 | 0.10 |
| Cyclopentasiloxane | 1.80 | 1.80 | 1.80 | 1.80 | 1.80 | 1.80 |
| Preservatives | 0.18 | 0.18 | 0.18 | 0.18 | 0.18 | 0.18 |
| Sodium metabisulfite | 0.15 | 0.15 | 0.15 | 0.15 | 0.15 | 0.15 |
| 4-amino-2-hydroxytoluene (p-amino-o-cresol)PAOC | — | — | — | — | 0.70 | 0.70 |
| m-aminophenol: Rodol EG | 0.03 | — | — | — | — | — |
| o-aminophenol: Rodol 2G | 0.05 | 0.01 | 0.05 | 0.03 | 0.20 | 0.10 |
| p-aminophenol: Rodol P base | — | — | 0.05 | 0.03 | 0.20 | 0.30 |
| N,N Bis(2-hydroxyethyl)-p-phenylenediamine sulfate: HED | 0.13 | — | — | — | — | — |
| 2-methylresorcinol: RodolMRP | — | — | — | — | — | — |
| 1-Napthol: Rodol ERN | — | — | — | — | — | — |
| p-phenylenediamine: Rodol D type J | 0.70 | 0.35 | 0.02 | 0.01 | 0.15 | 0.03 |
| Resorcinol: Rodol RS | 0.35 | 0.45 | 0.03 | 0.01 | 0.03 | 0.03 |
| Phenyl methyl pyrozolone(Rodol PMP | — | 0.01 | — | — | — | — |
| HC Red #3 | — | — | — | — | 0.20 | 0.02 |
| Sodium hydroxide, liquid 50% active | 0.4–0.6 | 0.4–0.6 | 0.4–0.6 | 0.4–0.6 | 0.4–0.6 | 0.4–0.6 |
| Mixed pH = | 7.5–8.0 | 9.0–9.5 | 9.0–9.5 | 9.0–9.5 | 8.0–8.5 | 9.0–9.5 |

EXAMPLE #2

L'Oreal Dark Brown Permanent Hair Color

Color the hair tresses using L'Oreal dark brown permanent hair color. Follow the instruction sheet. Measure the change in color delta E using McBeth ColorEye.

The changes in Delta E values are summarized in below table. You can see from the results that change in color after one 30-min. treatment with L'Oreal Dark Brown is very similar to six-2-min. treatment of color conditioner. The good correlation was observed with number of treatment and change in the color of the hair. It takes six treatments to achieve a single 30 minutes treatment of permanent color.

| | L'Oreal's Preference: Dark Brown: Delta E | Invention: Dark Brown Delta E |
|---|---|---|
| 1 treatment—30 min. | 4.19 | |
| 2 treatments—2 min. each | | 1.68 |
| 4 treatments—2 min. each | | 3.45 |
| 6 treatments—2 min. each | | 4.02 |

It can be seen that six treatments of two minutes per each treatment with the dark brown color composition of the present invention, resulted in approximately the same color change, Delta E, as one thirty minute treatment with L'Oreal's dark brown color composition.

EXAMPLE #3

The combing experiment was been carried out to evaluate the extent of damage. Wet combing evaluation technique has been used to correlate damage. Lower wet combing force indicates less damage. The above tresses were evaluated via Instron to measure combing force.

Results indicated that the tresses treated with L'Oreal dark brown required much higher combing force than tresses treated with color conditioner.

Method for Using Compositions of the Invention

Shampoo the hair as usual. Pump the composition of the invention into the palm and mix. Apply product to the hair like a regular conditioner. Rinse the hands. Leave product in the hair for about 2 minutes for color maintenance to about 5 minutes for color change. Rinse the hair thoroughly.

Experimental

To evaluate the wet combing performance of a Dark Brown and Light Brown Color Conditioner of the invention the measurements below were made. The combing force of hair treated 30 times with Light Brown composition was measured and compare with combing force of hair treated with one treatment of L'Oreal Preference. Also, tensile strength damage caused by the composition of the invention was compared to tensile strength damage caused by a commercial color product (Preference by L'Oreal). Wet combing experiments have been carried out on the Instron 5500 series. All testing was carried out by applying 0.3 mL of product to bleached and waved 2 g hair tresses. Results are expressed in terms of the maximum load (highest force encountered during combing) and combing energy (area under the combing curve). Finesse extra moisturizer and Extra body have also been included in this study as internal controls. Wet combing results are given below.

Statistical analysis is presented in terms of the Tukey HSD test and the less rigorous LSD test.

| Treatment | Count | Mean | | Homogeneous Groups |
|---|---|---|---|---|
| Multiple Range Tests for M_Ld by Treatm | | | | |
| Method: 95.0 percent Tukey HSD | | | | |
| Comp. No. 23 | 8 | 9.14 | X | Comp. No. 23, Dark brown |
| Fin_M | 8 | 9.645 | X | Finesse Moisturizing |
| Fin_B | 8 | 13.5813 | X | Finesse Bodifying |
| Method: 95.0 percent LSD | | | | |
| Comp. No. 23 | 8 | 9.14 | X | Comp. No. 23, Dark brown |
| Fin_M | 8 | 9.645 | X | Finesse Moisturizing |
| Fin_B | 8 | 13.5813 | X | Finesse Bodifying |

-continued

| Treatment | Count | Mean | | Homogeneous Groups |
|---|---|---|---|---|
| Multiple Range Tests for T_Energy by Treatm | | | | |
| Method: 95.0 percent Tukey HSD | | | | |
| Comp. No. 23 | 8 | 8.40875 | X | Comp. No. 23, Dark brown |
| Fin_M | 8 | 9.35875 | X | Finesse Moisturizing |
| Fin_B | 8 | 12.4 | X | Finesse Bodifying |
| Method: 95.0 percent LSD | | | | |
| 3Comp. No. 23 | 8 | 8.40875 | X | Comp. No. 23, Dark brown |
| Fin_M | 8 | 9.35875 | X | Finesse Moisturizing |
| Fin_B | 8 | 12.4 | X | Finesse Bodifying |

The above data indicate that the combing force of Dark brown composition is very similar to the standard Finesse moisturizing conditioner. Higher combing force indicates difficult to comb.

Statistical analysis is presented in terms of the Tukey HSD test and the less rigorous LSD test.

| Treatm | Count | Mean | | Homogeneous Groups |
|---|---|---|---|---|
| Multiple Range Tests for Max_Ld by Treatm | | | | |
| Method: 95.0 percent Tukey HSD | | | | |
| Untreated | 8 | 19.4125 | X | Untreated |
| Rainbow 30x | 8 | 19.7013 | X | Invention Light Brown Conditioner 30x |
| L'Oreal | 8 | 53.4988 | X | L'Oreal Preference |
| Method: 95.0 percent LSD | | | | |
| Untreated | 8 | 19.4125 | X | Untreated |
| Invention 30x | 8 | 19.7013 | X | Invention Light Brown Conditioner 30x |
| L'Oreal | 8 | 53.4988 | X | L'Oreal Preference |

The above data indicate that the combing force of hair treated 30 times with Light brown composition is very similar to the untreated hair tresses. However, the combing force of hair treated with one treatment of L'Oreal is much higher than hair treated with Light Brown compositions. Again, as mentioned, higher combing force indicates difficult to comb and higher damage.

Tensile Testing

All tensile testing has been carried out on the Diastron MTT600. The tensile strength of approx. 50 individual fibers were measured for each treatment. The diameter of these individual fibers is measured prior to testing to allow the force to be normalized against cross sectional area.

That is: Stress=Force/Cross sectional area

The tensile properties of hair may be taken to reflect the extent of structural integrity. Various measurements may be used to assess these tensile properties. Common parameters include the stress at break, work to break or extension to break. The complex structural properties of hair dictate that the wet and dry tensile properties reflect the properties of different regions. Wet tensile properties may be regarded as being representative of the alpha helical keratin protein within the hair's microfibrils; while the dry tensile properties also includes a substantial contribution from the intercellular cement. Many previous sets of results have shown that changes in tensile properties as a function of a treatment are more often seen when considering the wet tensile properties. For this reason, these experiments represent measurement of the wet tensile properties of the various hair treatments.

Each set of crimped hair samples was soaked in water for 30 mins prior to testing. In addition, the slots in the tensile testing carousel were filled with water to ensure that the fibers remained soaked for the progression of the experiment. All tress treatments were carried out by the requester.

Break stress results are shown below.

Statistical analysis is again presented in terms of the Tukey HSD test and the less rigorous LSD test.

Multiple Range Tests for B_STRESS by TREATM

| TREATMENT | Count | Mean | Homogeneous Groups |
|---|---|---|---|
| Method: 95.0 percent Tukey HSD Break Stress (gm force/micron$^2$) | | | |
| L'OREAL | 45 | 0.0170723 | X L'Oreal Preference, Dark Brown |
| UNTREAT | 45 | 0.0182494 | X Untreated |
| Comp. No. 23 | 40 | 0.0185977 | X 3030-23 Invention-Dark Brown |
| Method: 95.0 percent LSD Break Stress (gm force/micron$^2$) | | | |
| L'OREAL | 45 | 0.0170723 | X L'Oreal Preference, Dark Brown |
| UNTREAT | 45 | 0.0182494 | X Untreated |
| Comp. No. 23 | 40 | 0.0185977 | X Comp. No. 23 Dark Brown |

The above results would seem to be suggesting that the chemical treatment L'Oreal Preference color has lowered the break stress, while the conditioner of the invention has had no effect on this tensile parameter remains as untreated. It indicates that hair treated with L'Oreal preference is easier to break compare to the untreated hair and the hair treated with conditioner of the invention.

The following is the example of formulation of Dark brown Coloring Shampoo:

Part A

| Item | Ingredients | Dark Brown |
|---|---|---|
| 1 | Deionized water | 60.00 |
| 2 | Polymer JR | 0.30 |
| 3 | Cocamidopropyl betaine | 7.00 |
| 4 | SCAP | 25.00 |
| 5 | DC-1870 HV | 0.08 |
| 6 | Propylene glycol | 0.30 |
| 7 | Versene 100 | 0.20 |
| 8 | Fragrance | 0.20 |
| 9 | Kathon CG(1.5% active) | 0.08 |
| 10 | DMDM hydantoin | 0.10 |
| 11 | Sodium metabisulfite | 0.15 |
| 12 | m-aminophenol: Rodol EG | 0.03 |
| 13 | o-aminophenol: Rodol 2G | 0.05 |
| 14 | N,N Bis(2-hydroxyethyl)-p-phenylenediamine sulfate: HED | 0.13 |
| 15 | p-phenylenediamine: Rodol D type J | 0.70 |
| 16 | Resorcinol: Rodol RS | 0.35 |
| 17 | Sodium hydroxide, liquid 50% active | 0.4–0.6 | pH = 7.5–8.0
Viscosity = 3000 to 6000 cps(spindle #4, 20 rpm)

Manufacturing Process
Weigh the ingredients (item#11 to 16) needed into an appropriate container
Flush the container (tank) with nitrogen gas
Add item#1 into a suitable container. Heat to 180–185 F., Keep the Nitrogen blanket
Add pre-weighed dyes with moderate agitation. Keep the Nitrogen blanket
Add item#2 with moderate agitation
Add item#3, and 4 dissolve completely
Mix batch at approximately 180–185 F. for at least an hour with agitation until particles are completely dissolved. Check for the particles
Begin cooling. Keep the nitrogen blanket with moderate agitation
At 130 F. add the Versene solution to the batch.
At 110 F. or below, add item#5, 6, 8, 9, 10, Mix well
Adjust the pH with item#17 to around 10.0 Keep the Nitrogen blanket through entire process
Qs with DI water Part B: Peroxide Shampoo

| Item # | Chemical Name | Actual Weight % |
|---|---|---|
| 1 | D.I. Water | 39.00 |
| 2 | Polymer JR 30M | 0.30 |
| 3 | Sodium C14-C16 Olefin Sulfonate | 35.00 |
| 4 | Lauramine oxide 29% | 3.70 |
| 5 | Lauryl alcohol | 0.50 |
| 6 | DC-1870 HV | 1.60 |
| 7 | DI water | 9.00 |
| 8 | DMDM Hydantoin 55% | 0.10 |
| 9 | Hydrogen peroxide, 35% | 10.00 |
| 10 | Fragrance | 0.20 |
| 11 | Phosphoric acid, 85% | 0.60 |

Specification:
pH = 2.7 to 3.0
Viscosity = 3000 to 6000 cps(spindle #4, 20 rpm)

Manufacturing Process
1. Add item#1 into a suitable container. Heat to 180–185 F.
2. Add item#2 with moderate agitation
3. At 165–170 F., add item#3, 4, 5,
4. Mix batch at approximately 160–165 F. for at least an hour with agitation until particles are completely dissolved. Check for the particles
5. Begin cooling.
6. At 110 F. or below, add item#6, 7, 8, 9, 10 Mix well
7. Adjust the pH with item#112.7 to 3.0
8. Qs with water The composition resulting from the mixing the developer composition; and the dye composition has a pH of greater than or equal to 7.5. This mixture is applied to the hair. After a period ranging from 2 to 30 minutes, the hair is rinsed with water, optionally treated with an after treatment composition, and the rinsed with water again.

The following mathematical formulas describe the color change results and the hair damage results, which are obtained through the use of the compositions and methods of the present invention.

Final color concentration
Change result=of dyestuff+pH+contact time+number of treatments.
Hair damage=(pH+concentration of oxidizing agent) times the contact time; with the proviso that when the contact time is about two minutes or less, then there is no appreciable hair damage no matter how high the number of treatments.

Thus, if the contact time is kept at about two minutes or below for each treatment with compositions of the invention then there is no appreciable hair damage no matter how many color application treatments according to the invention are preformed.

At the same time that hair damage is avoided by the methods of the invention, the consumer's hair is gradually being brought to the desired shade and color. This gradual change of color has two advantages: first, since the color is changed gradually, the consumer can stop the process if she does not like the color her hair is turning to. Second, some consumers do not want an abrupt change in color because they may feel embarrassed in public after having made such an abrupt change to the color of their hair. Moreover, the method and compositions of the present invention can be used in the shower, and on a daily basis, because the compositions and methods of the present invention, by contrast with current color compositions, do not employ poisonous levels of chemicals and also because compositions methods of the present invention involve hair application steps that are up to about two minutes in length. By contrast current hair coloring compositions require approximately 30 minutes' time for each application, an amount of time, which is clearly not suitable for use in the shower.

The methods of the present invention are not as messy as conventional permanent hair coloring methods. The methods of the present invention do not use chemical compositions that are as smelly and noxious as those used in conventional permanent hair-coloring methods. Because the methods of the invention can be carried out in the shower, they do not involve the dripping and the mess associated with conventional permanent hair coloring. The methods of the present invention do not use chemical compositions that can stain fixtures in the bathroom or that will stain the scalp and the face. Compositions 1 and 2 upon mixture form a composition with a pleasing viscosity and that is pleasing to the fingers. This is because one or both of compositions 1 and 2 contain a cationic conditioning agent.

A dual package which can be employed in the products and kits of the present invention is U.S. Pat. No. 6,082,588 to Markey et al which is hereby incorporated by reference.
Kit Containing an Instruction Sheet The invention also relates to a kit for carrying out the hair coloring method of the invention. The kit comprises a developer solution, a dye solution and a post treatment solution, each in a separate container or in a dual container, as described herein. The kit also contains written instructions that explain how the compositions of the invention are used.

The consumer admixes the components of the kit according to written instructions, to obtain the aqueous reaction mixture. The admixture may be conducted in a separate vessel external to the kit, or may take place in a container of the kit adapted to provide sufficient head space for mixing. The components that are mixed are the developer composition; the dye composition. The reactants may also be admixed on the hair of the user. Essentially upon mixing, reaction of the dye and the developer will commence. After treatment for a desired time the mixture of hair developer and hair dye is removed, preferably with water or a conventional shampoo or a conventional conditioning shampoo.

As noted above, dye intermediate composition and peroxygen composition are mixed together, and the resulting mixture is applied to the hair and allowed to remain for a set time, usually about 1 to about 2 minutes to about 1 hour or more preferably about 30 minutes to about 40 minutes.

Desired change in hair color by the method of the invention is described by the mathematical formula above. Desired change in hair color can be achieved in a number of other ways. In the first instance, the consumer can compare her hair color with desired hair color or the hair color of a sample tress. Hair dyeing by the method of the invention can be repeated until her hair color matches the desired hair color. It is noted that the compositions used in the methods of the invention have lower contact times and thus repeated use of these compositions will not cause hair damage. An unexpected discovery of the present invention is that for damage to hair to occur, contact time in each treatment must go above the threshold value of about two minutes. Thus, the consumer can lighten or color the hair through repeated applications wherein the duration of each color application is about two minutes or less. The following two advantages are thereby achieved: first, there is a stepwise approach to the desired color; and second, a minimum of hair damage is done.

By the method of the invention, durable desired hair color, with longer lasting hair condition, clean soft feel, and a minimum of hair damage is achieved.

In following the method of the invention, the consumer can compare the color of her hair with the desired hair color, which can be printed on the package of the product. The consumer can also vary the number of days of application of the product, and the consumer can also vary the amount of time the mixture of composition 1 and 2 is left in the hair on each application. The number of applications can vary from about 7 to about 30 applications. The time of each application can vary from about 1 to about two minutes.

The method of the invention occurs over the course of days. Therefore, the final color of the consumer's hair may be affected by the amount of exposure to the sun of the hair during the course of treatment.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art.

What is claimed is:

1. A method for permanently dyeing hair which comprises subjecting said hair to a number of treatments, having a set time interval between each two consecutive such treatments, wherein each treatment comprises:
   a.) contacting said hair for a period of about 5 seconds to about 3 minutes with a recently made mixture of:
      i.) an alkaline composition comprising a dye intermediate in a shampoo base or in a conditioner base; and
      ii.) an acidic composition comprising an oxidizing compound in a shampoo base or in a conditioner base;
   b.) rinsing said mixture from said hair with water;
with the proviso that when a conditioner base is present in a.) i.) above, an independently selected conditioner base is also present in a.) ii.) above; and when a shampoo base is present in a.) i.) above, an independently selected shampoo base is also present in a.) ii.) above;
and wherein said number of treatments with an identically formulated mixture is from 2 to about 30; and wherein said set time interval between each two consecutive treatments is between about 8 hours and 30 days.

2. A method according to claim 1, wherein said dye intermediate is selected from the group consisting of:
m-aminophenol;
p-phenylene diamine;
p-toluenediamine;
2-chloro-p-phenylenediamine;
N-phenyl-p-phenylenediamine;

N-2-methoxyethyl-p-phenylenediamine;
N,N-bis-(hydroxyethyl)-p-phenylenediamine;
2-hydroxymethyl-p-phenylenediamine;
2-hydroxyethyl-p-phenylenediamine;
4,4'-diaminodiphenylamine;
2,6-dimethyl-p-phenylenediamine;
2-isopropyl-p-phenylenediamine;
N-(2-hydroxypropyl)-p-phenylenediamine;
2-propyl-p-phenylenediamine;
1,3-N, N-bis-(2-hydroxyethyl)-N, N-bis (4-aminophenyl)-2-propanol;
2-methyl-4-dimethylaminoaniline;
p-aminophenol;
p-methylaminophenol;
3-methyl-p-aminophenol;
2-hydroxymethyl-p-aminophenol;
2-methyl-p-aminophenol;
2-(2-hydroxyethylaminomethyl)-p-aminophenol;
2-methoxymethyl-p-aminophenol;
5-aminosalicylic acid;
catechol; pyrogallol;
o-aminophenol;
2,4-diaminophenol;
2,4,5-trihydroxytoluene;
1,2,4-trihydroxybenzene;
2-ethylamino-p-cresol;
2,3-dihydroxynaphthalene;
5-methyl-o-aminophenol;
6-methyl-o-aminophenol;
2-amino-5-acetaminophenol;
2-methyl-1-naphthol;
1-acetoxy-2-methylnaphthalene;
1,7-dihydroxynaphthalene;
resorcinol; 4-chlororesorcinol;
1-naphthol;
1,5-dihydroxynaphthalene;
2,7-dihydroxynaphthalene;
2-methylresorcinol;
1-hydroxy-6-aminonaphthalene-3-sulfonic acid;
thymol (2-isopropyl-5-methylphenol);
1,5-dihydroxy-1,2,3,4-tetrahydronaphthalene;
2-chlororesorcinol;
2,3-dihydroxy-1,4-naphthoquinone;
1-naphthol-4-sulfonic acid;
m-phenylenediamine;
2-(2,4-diaminophenoxy)ethanol;
N,N-bis(hydroxyethyl)-m-phenylenediamine;
2,6-diaminotoluene;
N,N-bis(hydroxyethyl)-2,4-diaminophenetole;
bis(2,4-diaminophenoxy)-1,3-propane;
1-hydroxyethyl-2,4-diaminobenzene;
2-amino-4 hydroxyethylaminoanisole;
aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene;
2,6-bis(hydroxyethylamino) toluene;
2-hydroxy-4-carbamoylmethylaminotoluene;
m-carbamoylmethylaminophenol;
6-hydroxybenzomorpholine;
2-hydroxy-4-aminotoluene;
2-hydroxy-4-hydroxyethylaminotoluene;
4,6-dichloro-m-aminophenol;
2-methyl-m-aminophenol;
2-chloro-6-methyl-m-aminophenol;
2-hydroxyethoxy-5-aminophenol;
2-chloro-5-trifluoroethylaminophenol;
4-chloro-6-methyl-m-aminophenol;
N-cyclopentyl-3-aminophenol;
N-hydroxyethyl-4-methoxy-2-methyl-m-aminophenol;
5-amino-4-methoxy-2-methylphenol;
2-dimethylamino-5-aminopyridine;
2,4,5,6-tetra-aminopyrimidine;
4,5-diamino-1-methylpyrazole;
1-phenyl-3-methyl-5-pyrazolone;
6-methoxy-8-aminoquinoline;
2,6-dihydroxy-4-methylpyridine;
5-hydroxy-1,4-benzodioxane;
3,4-methylenedioxyphenol;
4-hydroxyethylamino-1,2-methylenedioxybenzene;
2,6-dihydroxy-3,4-dimethylpyridine;
5-chloro-2,3-dihydroxypyridine;
3,5-diamino-2,6-dimethoxypyridine;
2-hydroxyethylamino-6-methoxy-3-aminopyridine;
3,4-methylenedioxyaniline;
2,6-bis-hydroxyethoxy-3,5-diaminopyridine;
4-hydroxyindole;
3-amino-5-hydroxy-2,6-dimethoxypyridine;
5,6-dihydroxyindole;
7-hydroxyindole; 5-hydroxyindole;
2-bromo-4,5-methylenedioxyphenol;
6-hydroxyindole;
3-amino-2-methylamino-6-methoxypyridine;
2-amino-3-hydroxypyridine;
2,6-diaminopyridine;
5-(3,5-diamino-2-pyridyloxy)-1,3-dihydroxypentane;
3-(3,5-diamino-2-pyridyloxy)-2-hydroxypropanol
4-hydroxy-2,5,6-triaminopyrimidine;
or combinations thereof.

3. A method according to claim 1, wherein said conditioner base in a.) i.) comprises a conditioning agent independently selected from the group consisting of:
dicetyl dimonium chloride;
poly(dimethyldiallylammonium chloride);
Quaternium 57;
poly(dipropyldiallylammonium chloride);
poly(methyl-beta-propaniodiallylammonium choride);
poly(diallylpiperidinium chloride);
poly(vinylpyridinium chloride);
quaternised poly(vinyl alcohol);
quaternised poly (dimethylaminoethylmethacrylate);
poly (N-vinylpyrollidone);
poly(dimethylaminoethylmethacrylate);
poly(vinyl pyridine);
poly(ethyleneimine);
and mixtures thereof; and
wherein said conditioner base in a.) ii.) comprises a conditioning agent independently selected from the group consisting of:
dicetyl dimonium chloride;
poly(dimethyldiallylammonium chloride);
Quaternium 57;
poly(dipropyldiallylammonium chloride);
poly(methyl-beta-propaniodiallylammonium choride);
poly(diallylpiperidinium chloride);
poly(vinylpyridinium chloride);
quaternised poly(vinyl alcohol);
quaternised poly (dimethylaminoethylmethacrylate);
poly (N-vinylpyrollidone);
poly(dimethylaminoethylmethacrylate);
poly(vinyl pyridine) and poly(ethyleneimine);
and mixtures thereof.

4. A method according to claim 1, wherein said alkaline composition of a.) i.) prior to mixture with said acidic mixture of a.)ii.) has a pH of about 8 to about 10.

5. A method according to claim 1, wherein said acidic composition of a.) ii.) prior to mixture with said alkaline mixture of a.) i.) has a pH of about 3 to about 5.

6. A method according to claim 1 wherein said alkaline composition according to a.) i.) comprises:
   A.) from about 0.05% to about 1.0% of a dye intermediate;
   B.) from about 0.1% to about 0.5% of a coupler; and
   C.) from about 1% to about 90% of a conditioner base.

7. A method according to claim 1 wherein said acidic composition according to a.) ii.) comprises:
   A.) from about 1% to about 90% of a conditioner base;
   B.) from about 0.5% to about 2.5% of a volatile silicone; and
   C.) from about 0.1% to about 5% of an oxidative compound.

8. A method according to claim 1 wherein said period for contacting said hair is between about 1 minute and 3 minutes.

9. A method according to claim 1 wherein said set time interval is between about 1 day and about 3 days.

10. A method according to claim 1 wherein said hair is highlighted.

11. A method according to claim 1 wherein said hair has wet combing tensile strength maintained.

12. A method according to claim 1 wherein said hair is not significantly damaged.

13. A method according to claim 1 wherein said hair is conditioned.

14. A method according to claim 1 wherein said hair is shampooed.

15. A method according to claim 1 wherein said oxidative compound is selected from the group consisting of hydrogen peroxide, urea peroxide, melamine peroxide, sodium perborate and sodium percarbonate.

16. A method according to claim 1 wherein the first composition comprises from about 35% to about 98.9% water.

17. A method according to claim 1, wherein the mixture of part A and part B has a neat viscosity of from about 500 cps to about 60,000 cps at 26.7.degree. C., as measured by a Brookfield RVTDCP with a spindle CP-41 at 1 RPM for 3 minutes.

18. A method for maintaining hair color through the use of a permanent hair dye which comprises subjecting said hair to successive treatments, having a set time interval between each two consecutive such treatments, wherein each treatment comprises:
   a.) contacting said hair for a period of about 5 seconds to about 3 minutes with a recently made mixture of:
      i.) an alkaline composition comprising a dye intermediate in a shampoo base or in a conditioner base; and
      ii.) an acidic composition comprising an oxidating compound in a shampoo base or in a conditioner base;
   b.) rinsing said mixture from said hair with water;
with the proviso that when a conditioner base is present in a.) i.) above, an independently selected conditioner base is also present in a.) ii.) above; and when a shampoo base is present in a.) i.) above, an independently selected shampoo base is also present in a.) ii.) above;
and wherein said number of treatments is at least 2; and wherein said set time interval between each two consecutive treatments is between about 8 hours and 30 days.

19. A method according to claim 1 wherein said dye intermediate is present at about 0.1% to about 1%.

20. A method according to claim 1 wherein said oxidative compound is present at about 2% to about 5%.

21. A dispenser containing composition ai and aii for dispensing simultaneously composition a.) i.) and composition a.) ii.) according to claim 1, which comprises:
   A.) a means for holding composition a.) i.) and composition a.) ii.) in physically separate locations;
   B.) a means for protecting composition a.) i.) and composition a.) ii.) from air prior to dispensing;
   C.) a means for dispensing composition a.) i.) and composition a.) ii.) in equal amounts and in proximity to each other.

22. A method according to claim 1 wherein composition a.) i.) and composition a.) ii.) are mixed by hand.

23. A method according to claim 1 which comprises rinsing said mixture of composition a.) i.) and composition a.) ii.) from said hair with water in a shower.

* * * * *